United States Patent [19]

Bolton et al.

[11] Patent Number: 4,746,609
[45] Date of Patent: May 24, 1988

[54] RESTRICTION ENDONUCLEASE CLEAVING PALINDROMIC DNA

[75] Inventors: Bryan Bolton, Clayton-Le-Moors, Great Britain; Michael J. Comer, Bernried, Fed. Rep. of Germany; Christoph Kessler, Munich, Fed. Rep. of Germany; Georg Nesch, Raisting, Fed. Rep. of Germany

[73] Assignee: Boehringer Mannheim GmbH, Mannheim, Fed. Rep. of Germany

[21] Appl. No.: 742,800

[22] Filed: Jun. 10, 1985

[30] Foreign Application Priority Data

Jun. 13, 1984 [DE] Fed. Rep. of Germany ....... 3421937
Apr. 4, 1985 [DE] Fed. Rep. of Germany ....... 3512435

[51] Int. Cl.⁴ .................. C12P 19/34; C12N 9/22; C12R 1/025; C07H 21/04
[52] U.S. Cl. ..................................... 435/91; 435/199; 435/824; 536/27
[58] Field of Search .................. 435/91, 92, 199, 824; 536/27

[56] References Cited

PUBLICATIONS

Bolton, B. J., Nesch, G., Comer, M. J., Wolf, W. and Kessler, C. (1985) F.E.B.S. Letters 182(1), 130–134.
Roberts, R. J. (1985) Nucleic Acids Research 13 (suppl), r165.

Primary Examiner—Thomas G. Wiseman
Assistant Examiner—Charles L. Patterson, Jr.
Attorney, Agent, or Firm—Felfe & Lynch

[57] ABSTRACT

The present invention teaches restriction endonuclease Asp 718 which cleaves DNA in the palindromic recognition sequence at the sites indicated by the arrow:

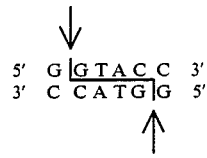

The endonuclease, obtained from Achromobacter species 718, DSM 2969, is useful in obtaining DNA fragments, e.g., for determining nucleotide sequences and other types of analysis of DNA.

4 Claims, No Drawings

RESTRICTION ENDONUCLEASE CLEAVING PALINDROMIC DNA

The present invention is concerned with a new Type II restriction endonuclease (Asp 718), with a process for obtaining it and with the use thereof.

Type II restriction endonucleases are endodesoxyribonucleases which recognise certain DNA sequences and are able to split at definite positions. Certain phosphodiester bridges are thereby hydrolysed in the target sequence, namely, one in each polynucleotide strand. Type II restriction endonucleases are, therefore, valuable for the analysis of DNA molecules.

Specific Type II restriction endonucleases are admittedly known for numerous DNA sequences but there is still a need for the provision of further Type II restriction endonucleases which cleave DNA sequences in those positions which hitherto have not been cleft by any of the known restriction endonucleases.

Therefore, it is an object of the present invention to provide a new restriction endonuclease which is able specifically to recognise a sequence and is able to cleave at a new position.

Thus, according to the present invention, there is provided a restriction endonuclease which is characterised by the palindromic recognition sequence

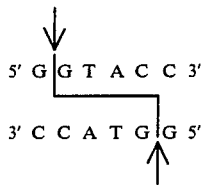

and by the cleavage position defined by the arrow.

The cleavage position is such that 5'-overhanging individual strand ends result. This makes possible a radio-active marking of the resulting fragments on the 5' end with the enzyme T4 polynucleotide kinase and also on the 3' end with the help of the enzyme Klenow polymerase. This is, for example, advantageous in the case of sequencing experiments.

The new Type II restriction endonuclease according to the present invention, hereinafter called Asp 718, has a temperature optimum of from 35° to 39° C. and a pH optimum at 8.5°/37° C. in tris/HCl buffer. Further optimum reaction parameters are 75 mmol/liter NaCl, 6 mmol/liter Mg$^{2+}$ and 6 mmol/liter 2-mercaptoethanol.

The presence of Mg$^{2+}$ is necessary for the activity of the enzyme.

As mentioned above, the enzyme acts upon palindromic sequences and thus recognises a self-complementary nucleic acid sequence in which the complementary strand of the double strand has the identical sequence in the counter direction.

The recognition sequence and the point of cleavage can be ascertained as follows:

The DNA of Virus SV40 (BRL) is linearised with Hpa II by cleavage at position 282. Both strands of this linearised DNA are terminally marked in two parallel, different reactions. The (−) strand is phosphorylated on the 5' end at position 284 with gamma-[$^{32}$P]-ATP and T4 polynucleotide kinase. In the second reaction, the complementary (+) strand is lengthened by one nucleotide on the 3' end at position 282 with alpha-[$^{32}$P]-dCTP and Klenow polymerase. Therefore, the marked (+) strand ends at position 283. Both differently marked DNAs are subsequently each split with Bgl I at position 5171. From each of the resultant 5'-and 3'-terminally marked fragments 4892(5')/4889(3') and 351(5')/354(3'), (length of the fragments referred to the marked individual strands) is respectively isolated the 351 bp (5') and 354 bp (3') fragment (position 5176 to 284(5'); position 5172 to 283(3')). The 5'-marked fragment is sequenced.

Additionally, in each case an aliquot of the isolated 351 bp (5') or 354 bp (3') fragments is split with the enzyme according to the present invention and the length of the 5'- and 3'-marked individual strands determined in the sequence gel by comparison with the 5'-sequence director. On the 5'-terminally marked (−) strand there is thereby given the cleavage position 234 and on the 3'-terminally marked (+) strand the cleavage position 230.

The length determination of the 5'-marked (−) individual strand of the Asp 718/Hpa II fragment is carried out in the following manner:

The (−)-individual strand 5'-marked on position 284 runs identically with the inner and thus 3'-positioned "G" on position 234 of the 5'-sequence director within the recognition sequence 5'-GGTACC-3'. Therefore, the 5'-marked individual strand terminates with the nucleotide G of the (−) strand at position 235 of the recognition sequence. The point of cleavage of Asp 718 on the 5'-marked (−) strand is thus between the nucleotide G at position 234 and G at position 235.

The length of the complementary 3'-marked (+) individual strand of the Asp 718/Hpa II fragment is determined analogously. The (+) individual strand 3'-marked at position 283 runs identically with the inner and thus 5'-positioned "C" at position 231 of the 5'-sequence director within the recognition sequence 5'-GGTACC-3'. The 3'-marked individual strand terminates, therefore, with the nucleotide G of the (+) strand at position 231 of the recognition sequence. The point of cleavage of Asp 718 on the 3'-marked (+) strand is thus between the nucleotide G at position 230 and G at position 231.

According to the present invention, Asp 718 is obtained by culturing Achromobacter species DSM 2969 and the enzyme obtained from the cells. For obtaining it, there can be used the conventional biochemical purification methods, whereby, in the particular fractions obtained, the presence of the enzyme can easily be detected on the basis of the cleavage of its recognition sequence. As substrate, there can be used, for example, lambda-DNA. The DNA fragments obtained are separated electrophoretically in agarose gel in the buffer systems conventional for the fragment separation in the presence of ethidium bromide.

The organism Achromobacter spec. DSM 2969 used for obtaining the enzyme grows aerobically in standard medium I, which is described hereinafter in detail in Example 1.

The organism is gram negative. The cells are colloidal (0.5 to 2.0 μm.) and are usually present individually. The temperature optimum is from 25° to 37° C. The doubling time is about 1 hour.

In a preferred embodiment of the process according to the present invention, the cells are digested, the extract is mixed with streptomycin sulphate until precipitation is complete, the precipitate is separated off and the supernatant is recovered.

For the digestion, there can be used the conventional mechanical and chemical methods, for example high pressure dispersion, ultrasonics or enzymatic digestion.

The high purification of the streptomycin supernatant containing the new enzyme preferably takes place by affinity chromatography, molecular sieve fractionation and via cation exchangers. As molecular sieve material, there has proved useful the product commercially available as Ultrogel ACA 34, which is an acrylamide/agarose heteropolymer of 3% acrylamide and 4% agarose.

As cation exchangers, there are preferably used phosphate group-containing substances, preferably carbohydrates, for example cellulose phosphate and the like. For the affinity chromatography, there has proved to be especially useful carrier-fixed heparin, for example heparin-sepharose CL 6 B (Pharmacia).

The following Examples are given for the purpose of illustrating the present invention:

EXAMPLE 1

Achromobacter species DSM 2969 is allowed to grow aerobically at 30° C. for 10 hours in standard medium I, which is described in detail hereinafter, and then harvested in the late logarithmic phase. 200 g. of the cell paste thus obtained (about 20 g. dry mass) are suspended in 500 ml. of digestion buffer (40 mmol/liter Tris/HCl, pH 7.6°/4° C.; 0,1 mmol/liter EDTA (ethylenediamine-tetraacetic acid); 7 mmol/liter 2-mercaptoethanol and 0.2 mmol/liter PMSF (phenylmethanesulphonyl fluoride)).

The cells are then digested twice by high pressure dispersion in a pre-cooled pressure cell at 1100 bar.

The digestion suspension is mixed with 10% streptomycin sulphate solution until precipitation is complete. After leaving to stand for 30 minutes at 4° C., the precipitate formed is centrifuged off for 120 minutes at 27300 g and discarded.

The standard medium I has the following composition:

| | |
|---|---|
| distilled water | 1000 ml. |
| special peptone | 15.6 g. |
| yeast extract | 2.8 g. |
| sodium chloride | 5.6 g. |
| glucose | 1.0 g. | pH 7.4 to 7.6
Fermentation conditions:
  150 liter Chemak fermenter
  100 liter working volume
  stirrer 450 r.p.m.
  air 0.08 Vvm
  temperature 30° C.
  amount of inoculum 10%
Yield: 60 g. of dry mass/100 liters of culture.

EXAMPLE 2

Streptomycin supernatant obtained according to Example 1 is chromatographed on an affinity chromatography column equilibrated with TEMG buffer (Heparinsepharose CL 6 B/5 cm.×28 cm.). After washing with four column volumes of TEMG buffer, the enzyme is eluted with a linear TEMG gradient with 0 to 1 mol/liter of sodium chloride. The enzyme elutes in the fractions with 0.45 to 0.6 mol/liter sodium chloride. The active fractions are combined and precipitated out with solid ammonium sulphate up to a degree of saturation of 80% (w/v). The precipitate is left to stand for 70 hours at 4° C.

The precipitate thus obtained is centrifuged off for 60 minutes at 27,300 g, taken up with TEMG buffer and applied to an Ultragel AcA-34 molecular sieve column with the dimensions 2×100 cm. This column is eluted with TEMG buffer+0.5 mol/liter sodium chloride and the eluate fractions with Asp 718 activity are combined.

The combined fractions are dialysed against TEMG buffer and chromatographed on a cation exchanger column equilibrated with TEMG buffer (cellulose phosphate P11/3×10 cm.). After washing with two column volumes of TEMG buffer, the enzyme is eluted with a linear TEMG gradient of 0 to 1 mol/liter sodium chloride. Asp 718 elutes between 0.4 and 0.6 mol/liter sodium chloride.

The active fractions are combined and dialysed against 20 mmol/liter Tris/HCl buffer, pH 7.6°/4° C.; 0.1 mmol/liter EDTA; 10 mmol/liter 2-mercaptoethanol; 100 mmol/liter sodium chloride; 100 μg./ml. bovine serum albumin (BSA) and 50% glycerol and stored at −20° C.

Activity about 5 MU Asp 718 (activity definition: 1 U=1 μg. lambda-DNA/hour at 37° C. completely split).

Activity determination

Into a mixture of 5 μl. incubation buffer, containing 0.03 mol/liter Tris/HCl buffer, pH 8.5°/37° C.; 0.03 mol/liter magnesium chloride; 0.375 mol/liter sodium chloride; 0.03 mol/liter 2-mercaptoethanol and 0.5 mg./ml. BSA are introduced 14 μl. water and 5 μl. lambda-DNA (4 OD/ml.), as well as 1 μl. Asp 718 solution (1 U/μl.; dilution with storage buffer).

The solution is incubated for 1 hour at 37° C., cooled on ice and mixed with 5 μl. of a cold stop solution containing 7 mol/liter urea, 20 wt./vol. % saccharose, 0.06 mol/1 EDTA and 0.01 wt./vol. % bromophenol blue. 10 μl. of this mixture are taken and mixed with 20 μl. of diluted stop solution (above stop solution diluted 1:3 v/v with 0.02 mol/liter EDTA). This solution is heated to 65° C. for 20 minutes, stopped by pouring on to ice and 20 μl. thereof separated electrophoretically on a 0.6% agarose gel in 16 hours at 50 V. The bands obtained are identified by comparison with appropriate DNA length standards.

We claim:

1. Method of obtaining DNA sequences which are characterized by terminal nucleotide sequences indicated by the arrows:

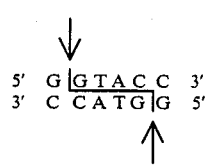

comprising contacting a DNA sample with endonuclease Asp 718 and $Mg^{2+}$ to cleave DNA at the sites indicated by the arrows.

2. Restriction endonuclease Asp 718, which cleaves DNA in a palindromic recognition sequence at a site indicated by the arrows:

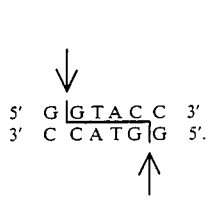

3. Restriction endonuclease according to claim 1 having a temperature optimum of from 35° to 39° C. and a pH optimum of 8.5 at a temperature of 37° C. in Tris/HCl buffer.

4. Restriction endonuclease of claim 3, wherein said endonuclease is obtained from Achromobacter species 718, DSM 2969.

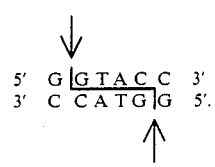

3. Restriction endonuclease according to claim 1 having a temperature optimum of from 35° to 39° C. and a pH optimum of 8.5 at a temperature of 37° C. in Tris/HCl buffer.

4. Restriction endonuclease of claim 3, wherein said endonuclease is obtained from Achromobacter species 718, DSM 2969.